United States Patent [19]

Anderson et al.

[11] Patent Number: 5,134,293

[45] Date of Patent: Jul. 28, 1992

[54] SCINTILLATOR MATERIAL

[75] Inventors: David F. Anderson, Batavia; Brian J. Kross, Aurora, both of Ill.

[73] Assignee: Universities Research Association, Inc., Washington, D.C.

[21] Appl. No.: 218,234

[22] Filed: Jul. 12, 1988

[51] Int. Cl.$^5$ .................... G01T 1/164; G01T 1/202
[52] U.S. Cl. ........................ 250/363.03; 250/484.1
[58] Field of Search ............ 250/483.1, 484.1, 363.03; 252/301.4 H

[56] References Cited

U.S. PATENT DOCUMENTS 2,254,956  9/1941  Aschermann et al. .
2,450,548  10/1948 Gislof et al. .
2,476,681  7/1949  Overbeek et al. .
4,510,394  4/1985  Allemand et al. ............... 250/483.1

FOREIGN PATENT DOCUMENTS 0143034  5/1985  European Pat. Off. ..... 252/301.4 H
61327    2/1948  Netherlands .

OTHER PUBLICATIONS

Blasse et al "Energy Transfer in . . . Cerium (III) Compounds", J. of Chem. Phys. vol. 51, No. 8 Oct. 1969, p. 3252.
"Luminescence of Cerium Compounds"-Kroger et al.-Jul. 1941.
Jacobson (ed.), Mar. 11, 1988, "Instrumentation in Positron Emission Tomography", Journal of the American Medical Association, vol. 259, No. 10.
Anonymous, Jun. 2, 1986, "PET penetrates inner sanctum of running engines", Design News.
Derenzo, 1986, "Recent developments in positron emission tomograpy (PET) instrumentaiton", Society of Optical Instrumentation Engineers vol. 671.
Phelps et al., May 17, 1985, "Positron Emission Tomography: Human Brain Function and Biochemistry", Science, vol. 228, No. 4701.
Fox, Apr. 13, 1984, "PET Scan Controversy Aired", Science, vol. 224.
Rasminsky, Jan. 1984, "Seen At Last: The Brain At Work", Reader's Digest.
Buchsbaum, Jul. 1983, "The Mind Readers", Psychology Today.
Derenzo et al., Feb. 1983, "High Resolution Positron Emission Tomography Using Small Bismuth Germanate Crystals And Individual Photosensors", IEEE Transactions on Nuclear Science, vol. NS-30, No. 1.
Oberg, Aug. 1982, "Window On The Brain", Science Digest.
Allemand et al., Jun. 11, 1982, "New Development in Fast Timing With BaF2 Scintillator", Communication, Laboratoire d'Electronique et de Technologie de l'Informatique (LETI/MCTE/82-245).
Ter-Pogrossian, Oct. 1980, "Positron Emission Tomography", Scientific American, vol. 243.
Allemand et al., 1980, "Potential Advantages of a Time-of-Flight Positron Camera"; The Journal of Nuclear Medicine, vol. 21, No. 2.
Heath et al. 1979, "Inorganic Scintillators: A Review of Techniques and Applications", Nuclear Instrumetns And Methods, vol. 162.

Primary Examiner—Janice A. Howell
Assistant Examiner—Richard Hang
Attorney, Agent, or Firm—Neuman, Williams, Anderson & Olson

[57] ABSTRACT

An improved scintillator material comprising cerium fluoride is disclosed. Cerium fluoride has been found to provide a balance of good stopping power, high light yield and short decay constant that is superior to known scintillator materials such as thallium-doped sodium iodide, barium fluoride and bismuth germanate. As a result, cerium fluoride is favorably suited for use as a scintillator material in positron emission tomography.

17 Claims, 3 Drawing Sheets

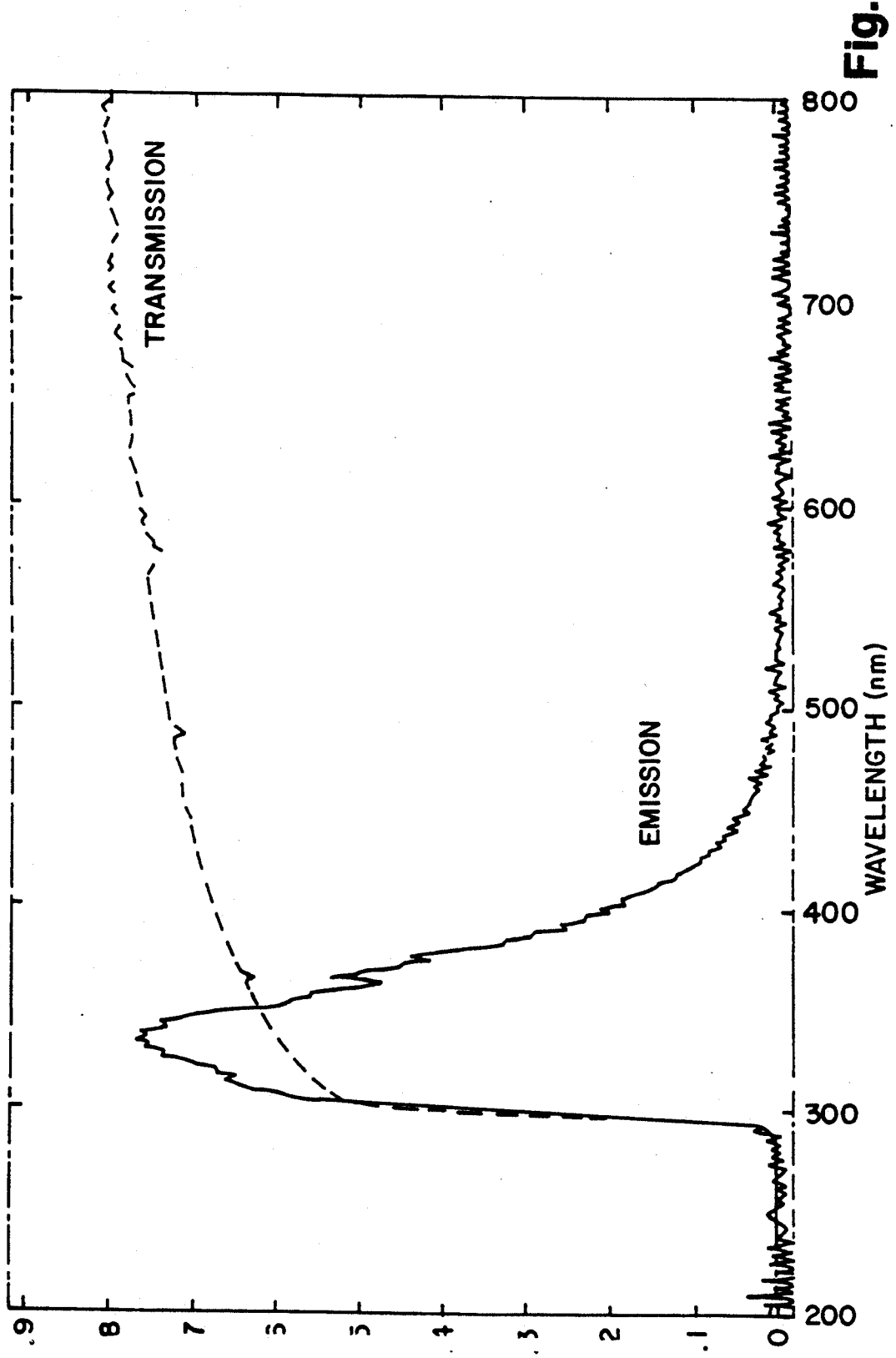

SCINTILLATOR MATERIAL

This invention was made with Government support under Contract No. DE-AC02-76CH03000, awarded by the United States Department of Energy. The Government has certain rights in the invention.

FIELD OF THE INVENTION

Scintillators are materials that emit flashes or pulses of light when they interact with ionizing radiation such as gamma rays. The present invention relates to the use of cerium fluoride ($CeF_3$) as a scintillator material. More particularly, the present invention relates to the use of cerium fluoride as a scintillator in photodetectors associated with positron emission tomography (PET).

BACKGROUND OF THE INVENTION

PET is a medical imaging technique in which a radioactively labeled substance is administered to a patient and then traced within the patient's body by means of an instrument that detects the decay of the isotope. In PET, a chemical tracer compound having a desired biological activity or affinity for a particular organ is labeled with a radioactive isotope that decays by emitting a positron (positive electron). The emitted positron loses most of its kinetic energy after traveling only a few millimeters in living tissue. It is then highly susceptible to interaction with an electron, an event that annihilates both particles. The mass of the two particles is converted into 1.02 million electron volts (1.02 MeV) of energy, divided equally between two 511 keV photons (gamma rays). The two photons are emitted simultaneously and travel in almost exactly opposite directions. The two photons penetrate the surrounding tissue, exit the patient's body, and are absorbed and recorded by photodetectors typically arranged in a circular array.

Biological activity within an organ under investigation can be assessed by tracing the source of the radiation emitted from the patient's body to the photodetectors. The source of the radiation can be accurately estimated by linking each photodetector with several other photodetectors on the opposite side of the photodetector array and registering a signal only if two detectors sense 511 keV photons coincidentally. When a coincidence is registered, an annihilation is recorded along a line connecting the two photodetectors. In this manner, a circumferential array of photodetectors can establish the sources of all coincident pairs of photons that originate within a volume defined by straight lines joining paired detectors. A computer program reconstructs the spatial distribution of the decaying isotopes within the patient. With suitable interpretation, PET images provide a noninvasive, regional assessment of many biochemical processes associated with human organs.

The value of PET as a clinical imaging technique is in large measure dependent upon the performance of the photodetectors. The typical PET camera comprises an array of photodetectors consisting of scintillator crystals coupled to photomultiplier tubes (PMTs). When a photon strikes a detector, it produces light in one of the scintillator crystals that is then sensed by the PMT, which registers the event by passing an electronic signal to the reconstruction processing circuitry. The scintillator crystals themselves must have certain properties, among which are (1) good stopping power, (2) high light yield and (3) fast decay time.

Stopping power is the ability to stop the 511 keV photons in as little material as possible so as to reduce the overall size of the photodetector, of which the scintillator crystals form a substantial portion. Stopping power is typically expressed as the linear attenuation coefficient (tau) having units of inverse centimeters ($cm^{-1}$). After a photon beam has traveled a distance "x" in a crystal, the proportion of photons that have not been stopped by the crystal is calculated as follows:

$$\text{fraction of unstopped photons} = e^{(-tau * x)}.$$

Thus, after traveling a distance of 1/tau (the "absorption length"), approximately 37% of the photons will not have been stopped; 63% will have been stopped. Likewise, 63% of the remaining photons will have been stopped after traveling an additional distance of 1/tau. For PET, one wants 1/tau to be as small as possible so that the photodetector is as compact as possible.

Light yield is also an important property of scintillators. Light yield is sometimes referred to as light output or relative scintillation output, and is typically expressed as the percentage of light output from a crystal exposed to a 511 keV photon beam relative to the light output from a crystal of thallium-doped sodium iodide, NaI(Tl), exposed to a 511 keV photon beam. Accordingly, the light yield for NaI(Tl) is defined as 100.

A third important property of scintillators is decay time. Scintillation decay time, sometimes referred to as the time constant or decay constant, is a measure of the duration of the light pulse emitted by a scintillator, and is typically expressed in units of nanoseconds (nsec). As noted above, in PET, the source of biological activity within an organ under investigation is determined by tracing the source of coincident photons emitted from the patient's body to the photodetectors. When two 511 keV photons are detected at the same time by a pair of photodetectors, the source of the photons is known to lie along the linear path connecting the two photodetectors. In general, only a fraction of the detected photons are in coincidence and thus used in the reconstruction analysis. Moreover, many false coincidences are registered because the finite decay time associated with each scintillator may cause it to emit light at the same time as another scintillator when in fact the photons inducing the light were slightly out of coincidence. For example, a photon arriving at one photodetector may produce a flash of light that does not decay (i.e., "turn off") until after a later photon, not in coincidence, produces a flash of light in a detector on the side opposite the first detector. In this instance, the flashes would overlap, and the photodetectors would register them as in coincidence. Thus, scintillator materials with long decay constants have an inherent problem in detecting coincident photons.

In addition to the problem of false coincidences, the positron emitting tracer compounds themselves typically have very short half-lives. In fact, most medical facilities performing PET also operate onsite accelerators to produce the short-lived radioactively labeled tracer compounds. Because of the short half-lives of these compounds, data on the occurrence of coincident photons needs to be gathered at as high a rate as possible. As noted above, the majority of the detected photons are not in coincidence, i.e., they are from sources outside the plane of the detector array. Consequently, if a scintillator's decay constant is short, then more of its time will be available for the detection of coincident photons.

In addition to the three important properties discussed above, scintillator crystals for PET should be easy to handle. For example, certain known scintillators are very hygroscopic, i.e., they retain moisture, making it necessary to very tightly encapsulate them to allow their use as scintillators in PET. These hygroscopic scintillators are expensive and difficult to use.

Known scintillator materials include (1) plastic scintillators, (2) thallium-doped sodium iodide (NaI(Tl)), (3) cesium fluoride (CsF), (4) bismuth germanate ($Bi_4Ge_3O_{12}$, also referred to as "BGO"), and (5) barium fluoride ($BaF_2$). Of these five scintillators, only the latter two, BGO and $BaF_2$, are used routinely for PET.

Plastic scintillators, typically composed of polystyrene doped with a wavelength-shifting additive, are commercially available under such trade names as PILOT U and NE 111. Upon excitation with a 511 keV photon, plastic scintillators emit a light pulse having a very fast decay constant of approximately 1.5 nsec and light output proportional to the energy of the incident photon. The main disadvantage of plastic scintillators is their low density (approximately 1.1 to 1.2 $g/cm^3$) due to the light atoms (hydrogen and carbon) that make up the molecules of the material. Because of their low density, plastic scintillators have poor stopping power, and are therefore poorly suited for use in PET.

NaI(Tl), thallium-doped sodium iodide, has the best light output of the five scintillators listed above. NaI(Tl) also has reasonably good stopping power (1/tau=3.0 cm at 511 keV). However, NaI(Tl) has a long decay constant (250 nsec), a significant disadvantage for use in PET. NaI(Tl) has an additional disadvantage: it is highly hygroscopic, making it extremely difficult to handle in that it must be tightly encapsulated in bulky cans.

CsF, cesium fluoride, has an advantage over plastic scintillators because of its relatively high density (4.61 $g/cm^3$) and consequent stopping power. However, the light output and decay constant of CsF are inferior to those of plastic scintillators. CsF is also highly hygroscopic, well above NaI(Tl) which, as noted above, makes it expensive and difficult to handle.

BGO has the highest density (7.13 $g/cm^3$) of the five known scintillator materials listed above. Its stopping power is the best of the five materials (1/tau=1.1 cm at 511 keV). As a result, BGO is best able to absorb 511 keV photons efficiently in small crystals. However, BGO's very long delay constant (300 nsec), longer even than NaI(Tl), is a significant disadvantage for use in PET.

The use of $BaF_2$ as a scintillator material is described in Allemand et al. U.S. Pat. No. 4,510,394. $BaF_2$ emits light having two components: a slow component having a decay constant of approximately 620 nsec and a fast component having a decay constant of approximately 0.6 nsec. $BaF_2$ has a light yield of approximately 16% that of NaI(Tl) and about half the stopping power of BGO (1/tau=2.3 cm at 511 keV). Unlike CsF and NaI(Tl), $BaF_2$ is not hygroscopic.

The fast component of $BaF_2$ emits light in the ultraviolet region of the spectrum. Glass photomultiplier tubes are transparent to ultraviolet light, so a quartz photomultiplier tube must instead be used to detect the fast component of $BaF_2$. Since quartz photomultiplier tubes are substantially more expensive than glass, one would prefer to avoid using $BaF_2$, if possible, in favor of using a scintillator that can be detected by a glass photomultiplier tube. The fast component gives $BaF_2$ very good timing resolution, but the slow component limits its high rate capabilities. In other words, it takes longer for $BaF_2$ to get ready for the next event.

Of the known scintillator materials, BGO has the best stopping power, NaI(Tl) has the best light yield, and $BaF_2$ has the best timing resolution. However, as noted above, some of these materials have significant shortcomings which hinder their performance as scintillators for PET: BGO has a very long decay constant; NaI(Tl) also has a very long decay constant and is hygroscopic. Of these materials, $BaF_2$ has the best balance of stopping power, light output and decay constant, and does not present a problem with hygroscopy. However, the slow component of $BaF_2$ does limit its rate capabilities.

OBJECTS OF THE INVENTION

It is therefore an object of the invention to provide an improved scintillator material.

Another object of the invention is to provide a scintillator material having enhanced utility in PET.

A further object of the invention is to provide a scintillator material having a superior balance of stopping power, light yield and decay constant.

SUMMARY OF THE INVENTION

The above objects are accomplished by a scintillator material comprising cerium fluoride. Cerium fluoride has been found to provide a balance of stopping power, light yield and decay constant that is superior to known scintillator materials. As a result, cerium fluoride is favorably suited for use as a scintillator material in positron emission tomography.

BRIEF DESCRIPTION OF THE DRAWINGS

FIG. 4 is a graph showing the relative amount of light emitted (solid line) and transmitted (broken line) by wavelength from a cerium fluoride scintillator crystal.

DETAILED DESCRIPTION OF THE PREFERRED EMBODIMENTS

Figure 1:
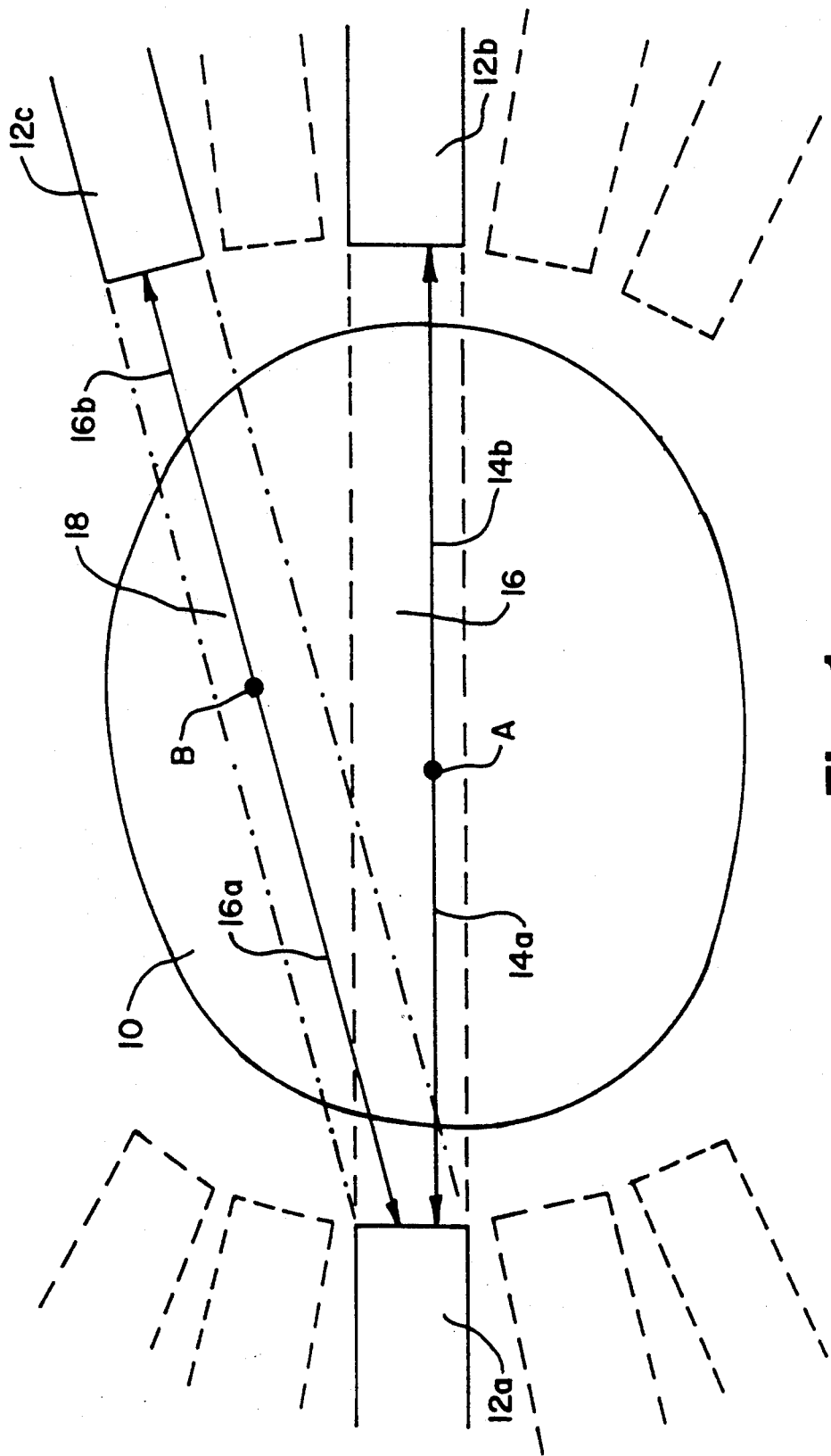
FIG. 1 is a schematic diagram showing the basic mechanism of positron emission tomography.

Turning first to FIG. 1 of the drawings, an object 10, such as, for example, a section of a human brain, is shown in cross-section for study using PET. Object 10 is placed between two arrays of oppositely disposed photodetectors, three of which are illustrated for simplicity in FIG. 1 as detectors 12a, 12b and 12c. A radioactively labeled substance having an affinity for object 10 is administered to the patient. The substance decays by emitting a positron (not illustrated), which slows and interacts with electrons (not illustrated) in the tissue of object 10. This positron/electron interaction causes the annihilation of both particles at point A in FIG. 1, producing two 511 keV photons, illustrated as rays 14a and 14b, which are emitted approximately 180 degrees to each other. If rays 14a and 14b are detected simultaneously (in coincidence) by detectors 12a and 12b, then the decay is localized to the space 16 between detectors 12a and 12b.

Positron/electron annihilations occurring elsewhere in the patient such as at point B will be detected by another pair of photodetectors. Thus, if rays 16a and 16b in FIG. 1 are detected simultaneously by detectors 12a and 12c, the decay is localized to the space 18 between detectors 12a and 12c. In this manner, the source of photons emitted from within object 10 can be accurately established.

Figure 2:
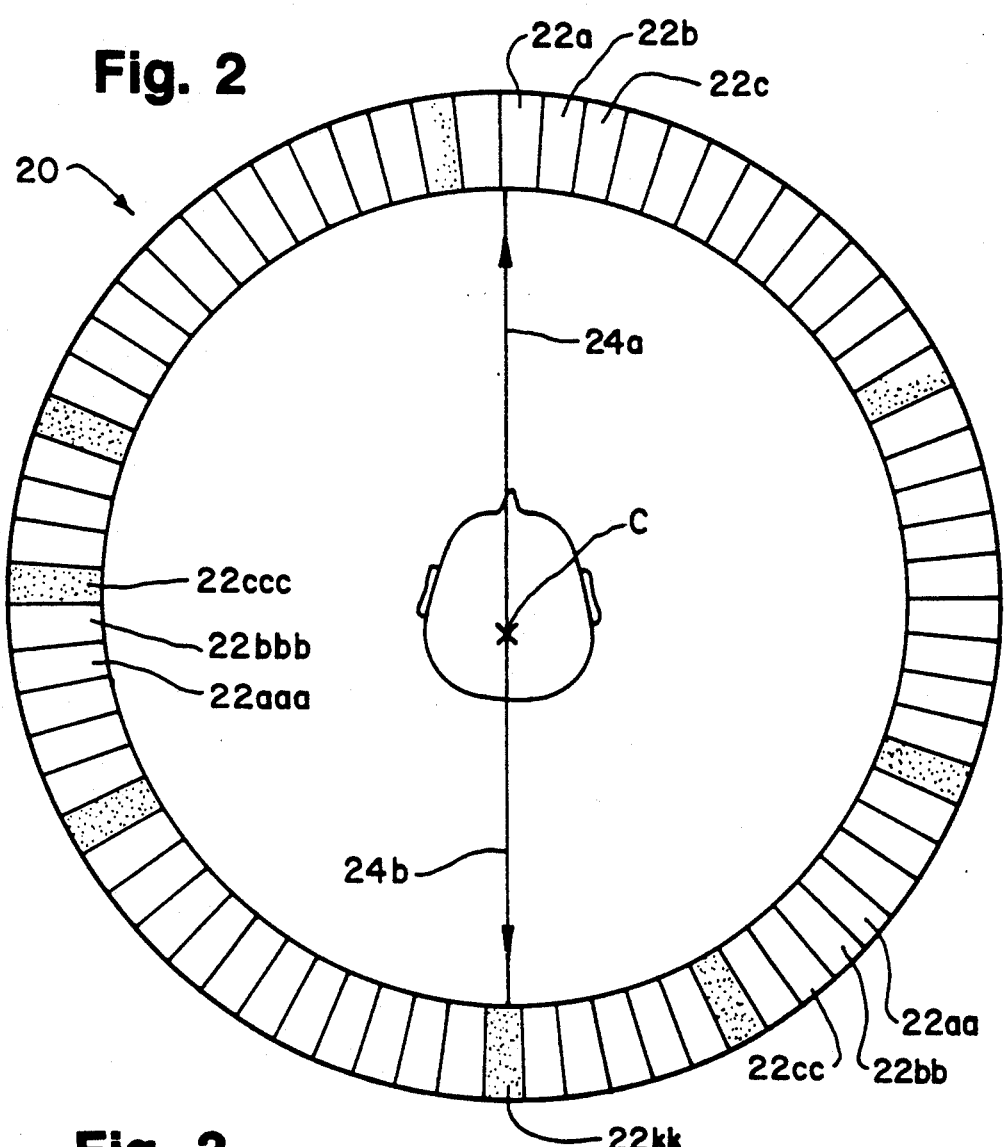
FIG. 2 is a schematic diagram of a PET camera showing a circular array of photodetectors.

FIG. 2 illustrates a ring or circular array 20 of detectors 22a, 22b, 22c, etc., used to localize the source of coincident 511 keV photons. Detectors 22a, 22b, 22c, etc., are arranged so that only simultaneous events occurring on the opposite side of ring 20 are recorded. For example, an annihilation at point C will produce two 511 keV photons, illustrated in FIG. 2 as rays 24a and 24b. If rays 24a and 24b are detected simultaneously by two detectors, for example detectors 22a and 22kk in FIG. 2, then the event is recorded. A computer program reconstructs the spatial distribution of the decaying isotopes within the patient by back-projecting the recordings of simultaneous events by detectors located on nearly opposite sides of the ring.

Figure 3:
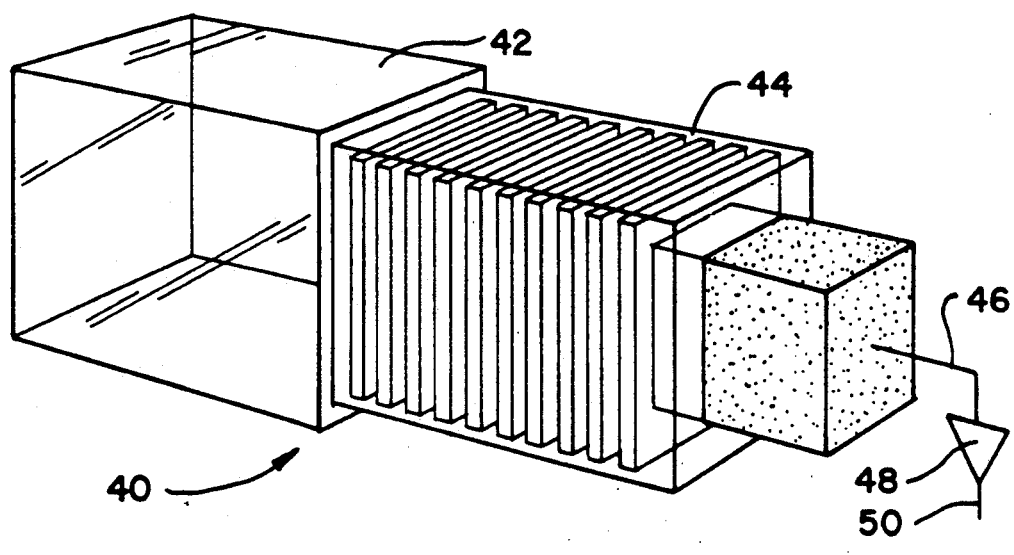
FIG. 3 is a schematic diagram of a typical PET photodetector showing the arrangement of a scintillator crystal and a photomultiplier tube.

A typical PET photodetector 40 is illustrated schematically in FIG. 3. In photodetector 40, scintillator crystal 42 is coupled to photomultiplier tube 44. Photomultiplier tube 44 is coupled by wires (one of which is designated for simplicity as wire 46) to amplifier 48 which in turn passes the signals to the reconstruction circuitry via wire 50.

A scintillator crystal comprising cerium fluoride ($CeF_3$) has been found to possess favorable stopping power, light yield and decay constant for use as a scintillator material in PET photodetectors such as that illustrated in FIG. 3. The relevant properties of $CeF_3$ are compared to those of known scintillator materials in the following table.

TABLE I

|  | $CeF_3$ | NaI(Tl) | $BaF_2$ | BGO |
|---|---|---|---|---|
| Decay Constant (nsec) | 5/27 | 250 | 0.6/620 | 300 |
| Light Yield | 4 | 100 | 16 | 8 |
| 1/tau (cm at 511 keV) | 1.9 | 3.0 | 2.3 | 1.1 |
| Hygroscopic | No | Very | Slightly | No |

As shown in Table I, $CeF_3$ provides a balance of stopping power, light yield and decay constant that is superior to other known scintillator materials. In particular, $CeF_3$ exhibits a fast component having a decay constant of less than approximately 5 nsec and a slow component having a decay constant of approximately 27 nsec, both far superior to those of NaI(Tl) and BGO. With respect to light yield, $CeF_3$ exhibits a value of 4 percent that of NaI(Tl); its light yield is thus about one-half that of BGO. In addition, the stopping power of $CeF_3$ (1/tau=1.9 cm at 511 keV) is between that of BGO and $BaF_2$. Finally, $CeF_3$ exhibits no hygroscopy.

As shown in Table I, in contrast to NaI(Tl), $CeF_3$ is superior in that its decay constant is far shorter than that of NaI(Tl) and it is not hygroscopic, making it much easier to handle than NaI(Tl).

As further shown in Table I, in contrast to $BaF_2$, $CeF_3$ has superior stopping power (1/tau) but an inferior light yield. In addition, $CeF_3$ has a fast component like $BaF_2$. Moreover, while the fast component of $BaF_2$ can only be detected using expensive quartz photomultiplier tubes, the fast component of $CeF_3$ can be detected using less expensive glass photomultiplier tubes.

Finally, as shown in Table I, in contrast to BGO, $CeF_3$ has an inferior stopping power (1/tau) and light yield, and a far superior decay constant. Thus, $CeF_3$ provides adequate stopping power and light yield with an improved decay constant.

The emission and transmission spectra of substantially pure $CeF_3$ are shown in FIG. 4. The emission spectrum of pure $CeF_3$ shows emission in the wavelength range of about 300 nm to about 500 nm, with a peak at about 340 nm. With emission between 300 nm and 500 nm, most of the light can be detected efficiently by glass photomultiplier tubes. Photomultiplier tubes made of ultraviolet transmitting glass, which adds little to their cost, gives an increase in the amount of light detected. The transmission spectrum of pure $CeF_3$ shows transmission in the wavelength range of about 300 nm and above, indicating that $CeF_3$ is transparent to its own radiation.

In addition to the discovery that substantially pure $CeF_3$ exhibits favorable scintillation properties, it has been found that $CeF_3$ doped with certain additives also provides improved scintillator materials. In general, such dopants can (1) effect a shift in the location of the wavelength peak of the emission spectrum, (2) lower the decay constant, or (3) increase the light yield of the material. For example, a $CeF_3$ crystal containing 2.0% terbium fluoride ($TbF_3$) produced an emission spectrum having a wavelength peak at about 535 nm and high light output. A $CeF_3$ crystal containing 0.2% chromic fluoride ($CrF_3$) produced an emission spectrum having a wavelength peak at about 350 nm and high light output. Other effective scintillator materials are $CeF_3$ doped with additives in the form $XF_3$, where X is a trivalent element selected from the group comprising chromium (Cr), praseodymium (Pr), terbium (Tb) and erbium (Er). $CeF_3$ containing dopant levels in the range of about 0.5 percent to about 1.0 percent by weight of the total scintillator material present have been found to be effective scintillators.

While particular embodiments and applications of the present invention have been shown, it will be understood, of course, that the invention is not limited thereto since modifications may be made by those skilled in the art, particularly in light of the foregoing teachings. It is therefore contemplated by the appended claims to cover any such modifications as incorporate those features which come within the true spirit and scope of the invention.

What is claimed is:

1. A scintillator comprising cerium fluoride wherein said scintillator is used in positron emission tomography.

2. The scintillator of claim 1 further comprising a scintillation-enhancing dopant wherein said dopant is a fluoride represented by the formula $XF_3$, wherein X is selected from the group consisting of chromium, praseodymium, terbium and erbium.

3. The scintillator of claim 2 wherein said dopant present in an amount ranging from about 0.5 percent to about 1.0 percent by weight of the scintillator.

4. A scintillator consisting essentially of cerium fluoride wherein said scintillator is used in positron emission tomography.

5. The scintillator of claim 4 further comprising a scintillation-enhancing dopant wherein said dopant is a fluoride represented by the formula $XF_3$, wherein X is selected from the group consisting of chromium, praseodymium, terbium and erbium.

6. The scintillator of claim 5 wherein said dopant is present in an amount ranging from about 0.5 percent to about 1.0 percent by weight of the scintillator.

7. A camera for use in position emission tomography comprising cerium fluoride as a scintillator.

8. The camera of claim 7 further comprising a photomultiplier tube coupled to said scintillator.

9. The camera of claim 7 wherein said scintillator further comprises a scintillation-enhancing dopant.

10. The camera of claim 9 wherein said dopant is a fluoride represented by the formula $XF_3$, wherein X is selected from the group consisting of chromium, praseodymium, terbium and erbium.

11. The camera of claim 10 wherein said dopant is present in an amount ranging from about 0.5 percent to about 1.0 percent by weight of the scintillator.

12. The method of detecting ionizing radiation which comprises using a scintillator comprising cerium fluoride, said scintillator further comprising a scintillation-enhancing dopant wherein said dopant is a fluoride represented by the formula $XF_3$, wherein X is selected from the group consisting of chromium, praseodymium, terbium and erbium.

13. The method of claim 12 wherein said dopant is present in an amount ranging from about 0.5 percent to about 1.0 percent by weight of the scintillator.

14. The method of performing positron emission tomography which comprises using photodetectors comprising cerium fluoride as a scintillator.

15. The method of claim 13 wherein said scintillator further comprises a scintillation-enhancing dopant.

16. The method of claim 14 wherein said dopant is a fluoride represented by the formula $XF_3$, wherein X is selected from the group consisting of chromium, praseodymium, terbium and erbium.

17. The method of claim 15 wherein said dopant is present in an amount ranging from about 0.5 percent to about 1.0 percent by weight of the scintillator.

* * * * *